US011529180B2

(12) United States Patent
Russell et al.

(10) Patent No.: US 11,529,180 B2
(45) Date of Patent: Dec. 20, 2022

(54) REVERSIBLE PIN DRIVER

(71) Applicant: McGinley Engineered Solutions, LLC, Casper, WY (US)

(72) Inventors: Matthew Russell, Casper, WY (US); Ben Warren, Casper, WY (US); Adam M. Johnson, Casper, WY (US); Joseph C. McGinley, Casper, WY (US); Connor Wetzel, Casper, WY (US)

(73) Assignee: McGinley Engineered Solutions, LLC, Casper, WY (US)

( * ) Notice: Subject to any disclaimer, the term of this patent is extended or adjusted under 35 U.S.C. 154(b) by 255 days.

(21) Appl. No.: 16/994,980

(22) Filed: Aug. 17, 2020

(65) Prior Publication Data

US 2021/0045790 A1    Feb. 18, 2021

Related U.S. Application Data

(60) Provisional application No. 62/888,125, filed on Aug. 16, 2019.

(51) Int. Cl.
*A61B 17/88* (2006.01)
*A61B 17/92* (2006.01)
*A61B 90/00* (2016.01)

(52) U.S. Cl.
CPC ...... *A61B 17/8883* (2013.01); *A61B 17/8861* (2013.01); *A61B 17/8888* (2013.01); *A61B 17/921* (2013.01); *A61B 90/39* (2016.02); *A61B 2090/3937* (2016.02)

(58) Field of Classification Search
CPC ................. A61B 17/8861; A61B 17/921
See application file for complete search history.

(56) References Cited

U.S. PATENT DOCUMENTS

| 1,831,813 A | 11/1931 | Levedahl |
| 2,883,891 A | 4/1959 | Robinson et al. |

(Continued)

FOREIGN PATENT DOCUMENTS

| DE | 102011056927 A1 | 6/2013 |
| WO | 9724991 A1 | 7/1997 |

(Continued)

*Primary Examiner* — Nicholas W Woodall
(74) *Attorney, Agent, or Firm* — Holzer Patel Drennan

(57) ABSTRACT

An implant driver for engaging an orthopedic implant for selective advancement and retraction of the implant. The implant driver includes a first jaw assembly comprising a helical cam surface corresponding with a first direction of rotation. The first jaw assembly is operative to engage, in response to rotation in the first direction, the implant using spherical jaw members disposed in constrictive helical channels. The implant driver includes a second jaw assembly comprising a helical cam surface corresponding with a second direction of rotation. The second jaw assembly is operative to engage, in response to rotation in the second direction, the implant using spherical jaw members disposed in constrictive helical channels. Absent rotation of the first and second jaw assemblies, the spherical jaws may not restrict relative axial movement between the implant and the implant driver to allow for advancement and/or retraction of the instrument relative to the implant.

13 Claims, 9 Drawing Sheets

(56) References Cited

U.S. PATENT DOCUMENTS

| | | | |
|---|---|---|---|
| 3,049,018 A * | 8/1962 | Lusskin | A61B 17/1624 |
| | | | 408/124 |
| 3,804,544 A | 4/1974 | Adams | |
| 4,014,621 A | 3/1977 | Johnson et al. | |
| 4,063,356 A | 12/1977 | Hepworth | |
| 4,140,111 A * | 2/1979 | Morrill | A61B 17/1697 |
| | | | 606/104 |
| 4,157,231 A | 6/1979 | Phillips | |
| 4,310,269 A | 1/1982 | Neu et al. | |
| 4,329,092 A | 5/1982 | Ponitzsch et al. | |
| 4,329,095 A | 5/1982 | Schmuck | |
| 4,644,335 A | 2/1987 | Wen | |
| 4,710,075 A | 12/1987 | Davison | |
| 4,723,911 A | 2/1988 | Kurtz | |
| 4,765,333 A | 8/1988 | Bray | |
| 4,867,158 A | 9/1989 | Sugg | |
| 4,951,690 A | 8/1990 | Baker | |
| 5,013,194 A | 5/1991 | Weinhold | |
| 5,014,793 A | 5/1991 | Germanton et al. | |
| 5,022,798 A | 6/1991 | Eckman | |
| 5,071,293 A | 12/1991 | Wells | |
| 5,133,728 A | 7/1992 | Petersen | |
| 5,139,376 A | 8/1992 | Pumphrey | |
| 5,161,921 A | 11/1992 | Corsi | |
| 5,277,799 A | 1/1994 | Bransch | |
| 5,361,504 A | 11/1994 | Huang | |
| 5,380,333 A | 1/1995 | Meloul et al. | |
| 5,411,503 A | 5/1995 | Hollstein et al. | |
| 5,533,842 A | 7/1996 | Johnson et al. | |
| 5,538,423 A | 7/1996 | Coss et al. | |
| 5,584,838 A | 12/1996 | Rona et al. | |
| 5,599,142 A | 2/1997 | Fujimoto et al. | |
| 5,613,810 A | 3/1997 | Bureller | |
| 5,810,828 A | 9/1998 | Lightman et al. | |
| 5,902,306 A | 5/1999 | Norman | |
| 5,961,257 A | 10/1999 | Bettini et al. | |
| 5,980,248 A | 11/1999 | Kusakabe et al. | |
| 6,033,409 A | 3/2000 | Allotta | |
| 6,081,741 A | 6/2000 | Hollis | |
| 6,096,042 A | 8/2000 | Herbert | |
| 6,342,057 B1 | 1/2002 | Brace et al. | |
| 6,494,590 B1 | 12/2002 | Paganini | |
| 6,527,778 B2 | 3/2003 | Athanasiou et al. | |
| 6,587,184 B2 | 7/2003 | Wursch et al. | |
| 6,665,948 B1 | 12/2003 | Kozin et al. | |
| 6,786,683 B2 | 9/2004 | Schaer et al. | |
| 6,925,725 B2 | 8/2005 | Herrmann et al. | |
| 7,073,989 B2 | 7/2006 | Erickson et al. | |
| 7,185,998 B2 | 3/2007 | Oomori | |
| 7,220,088 B2 | 5/2007 | Ferrari et al. | |
| 7,235,940 B2 | 6/2007 | Bosch et al. | |
| 7,314,048 B2 | 1/2008 | Couture et al. | |
| 7,482,819 B2 | 1/2009 | Wuersch | |
| 7,578,642 B2 | 8/2009 | Fritsche et al. | |
| 7,681,659 B2 | 3/2010 | Zhang et al. | |
| 7,691,106 B2 | 4/2010 | Schenberger | |
| 7,840,253 B2 | 11/2010 | Tremblay | |
| 7,946,049 B1 | 5/2011 | Wilton | |
| 7,992,311 B2 | 8/2011 | Cerwin | |
| 8,092,457 B2 | 1/2012 | Oettinger | |
| 8,162,074 B2 | 4/2012 | Cook | |
| 8,167,518 B2 | 5/2012 | Mathis et al. | |
| 8,171,642 B2 | 5/2012 | Fritsche | |
| 8,317,437 B2 | 11/2012 | Merkley et al. | |
| 8,460,297 B2 | 6/2013 | Watlington | |
| 8,511,945 B2 | 8/2013 | Apkarian | |
| 8,734,153 B2 | 5/2014 | Arzanpour | |
| 8,821,493 B2 | 9/2014 | Anderson | |
| 8,894,654 B2 | 11/2014 | Anderson | |
| 8,925,169 B2 | 1/2015 | Schevers | |
| 8,970,207 B2 | 3/2015 | Baumgartner | |
| 9,022,949 B2 | 5/2015 | Herndon | |
| 9,114,494 B1 | 8/2015 | Mah | |
| 9,204,885 B2 | 12/2015 | McGinley | |
| 9,358,016 B2 | 6/2016 | McGinley | |
| 9,370,372 B2 | 6/2016 | McGinley | |
| 9,492,181 B2 | 11/2016 | McGinley | |
| 9,855,060 B2 | 1/2018 | Ardel | |
| 2001/0031919 A1 | 10/2001 | Strommer | |
| 2001/0047219 A1 | 11/2001 | Oden | |
| 2002/0165549 A1 | 11/2002 | Owusu-Akyaw et al. | |
| 2003/0049082 A1 | 3/2003 | Morrison | |
| 2003/0229351 A1 | 12/2003 | Tidwell | |
| 2004/0146367 A1 | 7/2004 | Gerhardt | |
| 2004/0179829 A1 | 9/2004 | Phillips et al. | |
| 2004/0215395 A1 | 10/2004 | Strasser | |
| 2005/0116673 A1 | 6/2005 | Carl | |
| 2005/0131415 A1 | 6/2005 | Hearn et al. | |
| 2005/0169717 A1 | 8/2005 | Field | |
| 2005/0261870 A1 | 11/2005 | Cramer | |
| 2006/0004371 A1 | 1/2006 | Williams et al. | |
| 2006/0008771 A1 | 1/2006 | Courvoisier | |
| 2006/0025677 A1 | 2/2006 | Verard | |
| 2006/0074292 A1 | 4/2006 | Thomson | |
| 2006/0241628 A1 | 10/2006 | Parak | |
| 2006/0258938 A1 | 11/2006 | Hoffman | |
| 2007/0030486 A1 | 2/2007 | Gelbart | |
| 2007/0035311 A1 | 2/2007 | Wuersch | |
| 2007/0041799 A1 | 2/2007 | Schaefer | |
| 2008/0119725 A1 | 5/2008 | Lloyd | |
| 2008/0167653 A1 | 7/2008 | Watlington | |
| 2008/0226409 A1 | 9/2008 | Hasenzahl | |
| 2008/0228195 A1 | 9/2008 | von Jako | |
| 2008/0243125 A1 | 10/2008 | Guzman | |
| 2008/0292416 A1 | 11/2008 | Kado et al. | |
| 2009/0131986 A1 | 5/2009 | Lee et al. | |
| 2009/0182226 A1 | 7/2009 | Weitzner | |
| 2009/0245956 A1 | 10/2009 | Apkarian et al. | |
| 2009/0299439 A1 | 12/2009 | Mire et al. | |
| 2009/0326537 A1 | 12/2009 | Anderson | |
| 2010/0114099 A1 | 5/2010 | Patwardhan | |
| 2010/0137874 A1 | 6/2010 | Kim et al. | |
| 2010/0239380 A1 | 9/2010 | Amirov et al. | |
| 2011/0020084 A1 | 1/2011 | Brett | |
| 2011/0060242 A1 | 3/2011 | Hausman | |
| 2011/0245831 A1 | 10/2011 | Giersch et al. | |
| 2011/0245832 A1 | 10/2011 | Giersch et al. | |
| 2011/0245833 A1 | 10/2011 | Anderson | |
| 2011/0301611 A1 | 12/2011 | Garcia | |
| 2012/0037386 A1 | 2/2012 | Cook | |
| 2012/0123418 A1 | 5/2012 | Giurgi | |
| 2012/0179070 A1 | 7/2012 | Pommer et al. | |
| 2012/0253348 A1 | 10/2012 | Arlettaz et al. | |
| 2013/0122466 A1 | 5/2013 | Connor | |
| 2013/0237811 A1 | 9/2013 | Mihailescu | |
| 2013/0304069 A1 | 11/2013 | Bono et al. | |
| 2013/0307529 A1 | 11/2013 | Baumgartner | |
| 2013/0327552 A1 | 12/2013 | Lovelass | |
| 2014/0039517 A1 | 2/2014 | Stryker | |
| 2014/0081659 A1 | 3/2014 | Nawana | |
| 2014/0107471 A1 | 4/2014 | Haider | |
| 2014/0275760 A1 | 9/2014 | Lee | |
| 2014/0275989 A1 | 9/2014 | Jacobsen | |
| 2014/0350685 A1 | 11/2014 | Bagga et al. | |
| 2015/0066030 A1 | 3/2015 | McGinley | |
| 2015/0066035 A1 | 3/2015 | McGinley | |
| 2015/0066036 A1 | 3/2015 | McGinley | |
| 2015/0066037 A1 | 3/2015 | McGinley | |
| 2015/0066038 A1 | 3/2015 | McGinley et al. | |
| 2015/0165580 A1 | 6/2015 | Holland | |
| 2016/0120553 A1 | 5/2016 | Xie | |
| 2016/0247276 A1 | 8/2016 | Chou | |
| 2017/0143396 A1 | 5/2017 | McGinley | |
| 2017/0345398 A1 | 11/2017 | Fuchs | |
| 2018/0070113 A1 | 3/2018 | Phillips | |
| 2018/0110572 A1 | 4/2018 | Flatt | |
| 2018/0260931 A1 | 9/2018 | Ozguner | |
| 2019/0209287 A1 | 7/2019 | Zenz-Olson | |

(56) References Cited

U.S. PATENT DOCUMENTS

2019/0254684 A1    8/2019  McGinley
2019/0254685 A1    8/2019  McGinley

FOREIGN PATENT DOCUMENTS

| WO | 2015006296 A1 | 1/2015 |
| WO | 2015034562 A1 | 3/2015 |
| WO | 2015014771 A3 | 4/2015 |
| WO | 2016207628 A1 | 12/2016 |

* cited by examiner

REVERSIBLE PIN DRIVER

CROSS-REFERENCE TO RELATED APPLICATIONS

The present application claims priority to U.S. Provisional Application No. 62/888,125 filed Aug. 16, 2019, entitled "REVERSIBLE PIN DRIVER," which is specifically incorporated by reference for all it discloses and teaches.

The present application is also related to U.S. patent application Ser. No. 15/336,202 filed Oct. 27, 2016, entitled "TECHNIQUES AND INSTRUMENTS FOR PLACEMENT OF ORTHOPEDIC IMPLANTS RELATIVE TO BONE FEATURES," which is specifically incorporated by reference for all that it discloses and teaches.

BACKGROUND

Often times it is necessary during orthopedic surgical operations to place an implant relative to a bone of a patient. Such orthopedic implants may include transcutaneous pins (e.g., intra medullary (IM) pins), wires (e.g., Kirschner wires (K-wires)), or other implants. For instance, such implants may be used for pin fixation of bones, in connection with skeletal traction, or for other purposes.

Powered orthopedic instruments are often used to place orthopedic implants. In this regard, powered orthopedic instruments utilize a chuck or driver to engage the orthopedic implant. Manipulation of the chuck or driver during surgery has disadvantages including reduced ergonomics for the surgeon, interference with coordinated measurement systems, increased surgical time, and, ultimately, reduced patient outcomes.

SUMMARY

In view of the foregoing, the present disclosure generally relates to an improved driver that facilitates engagement between a powered instrument and an orthopedic implant. Specifically, the implant driver described herein may facilitate engagement of an orthopedic implant in response to rotation of the implant driver. In an example, the implant driver may be retracted relative to the orthopedic implant in the absence of rotation of the implant driver but may grip the implant when under rotation to reduce or prevent relative axial movement between the driver and the implant. Rotation in a first direction may allow for advancement of the implant in a proximal direction. Rotation in a second direction opposite the first direction may allow for retraction of the implant in a distal direction.

One implementation of the present disclosure includes an implant driver engageable with a surgical instrument for use in placement of orthopedic implants relative to a bone of a patient. The driver includes a first cannulated passage extending continuously through the implant driver along a working axis. The first cannulated passage is sized to receive and extend about at least a portion of an orthopedic implant within the cannulated passage. The driver also includes a first jaw assembly. The first jaw assembly includes a plurality of first helical channels comprising a first constrictive helical cam surface with a first direction of constriction associated with a first direction of rotation of the implant driver and a plurality of first spherical jaw members each disposed within a respective one of the plurality of first helical channels such that at least a portion of each of the first spherical jaw members is at least partially extendable into the cannulated passage to engage the orthopedic implant. The driver also includes a second jaw assembly that includes a plurality of second helical channels comprising a second constrictive helical cam surface with a second direction of constriction associated with a second direction of rotation of the implant driver opposite the first direction of rotation and a plurality of second spherical jaw members each disposed within a respective one of the plurality of second helical channels such that at least a portion of each of the second spherical jaw members is at least partially extendable into the cannulated passage to directly engage the orthopedic implant. Upon rotational motion of the implant driver in the first direction of rotation, rotational motion of the first helical channels engage the first constrictive helical cam surface with the first spherical jaw members to urge the first spherical jaw members into direct engagement with the orthopedic implant. Additionally, upon rotational motion of the implant driver in the second direction of rotation, rotational motion of the second helical channels engage the second constrictive helical cam surface with the second spherical jaw members to urge the second spherical jaw members into direct engagement with the orthopedic implant.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein.

DETAILED DESCRIPTION

As described above, the present disclosure relates to instruments that are used to engage orthopedic implants (e.g., to assist in placement of the implant). For instance, the orthopedic implant may include a pin or wire that is placed in the bone of the patient using a powered instrument such as a drill or the like.

The use of orthopedic implants such as pins (e.g., IM pins) and/or wires (e.g., K-wires) may be used in a variety of orthopedic applications. The orthopedic implants may be used to provide traction to the bones of a patient. Moreover, the orthopedic implant may be placed to allow for induced motion of a bone (e.g., to provide alignment, rotation, or other manipulation of a bone). Furthermore, orthopedic implants may be used for fixation to secure fractured bone portions.

Examples of an implant driver are described herein wherein a user may not be required to impart an external force onto the implant driver to maintain engagement with an orthopedic implant such as through a lever or other manipulated control of the driver. Rather the implant driver may engage the implant in response to rotation of the implant driver by an instrument. Absent rotation of the implant driver, the instrument may be held in place, but moveable (e.g., axially relative to the implant driver) by a user.

In turn, the user may be more able to control the instrument because a more ergonomic grip with greater control of the instrument may be taken by the user without having to grasp an engagement lever or the like. Additionally, examples of the implant driver described herein may allow for the implant driver to engage an orthopedic implant to impart rotational motion thereto. However, when the implant driver is not rotated, the implant driver may be moveable relative to the orthopedic implant. This allows a surgeon to advance and withdraw the orthopedic implant relative to a bone of a patient while the implant driver is rotating, yet allows the implant driver to be engaged to preclude axial movement between the driver and the implant such that the instrument may be retracted relative to the implant when not rotating. As such, the instrument may be retracted relative to the implant to, for example, to allow the implant to be further advanced after the instrument is retracted.

Figure 1:
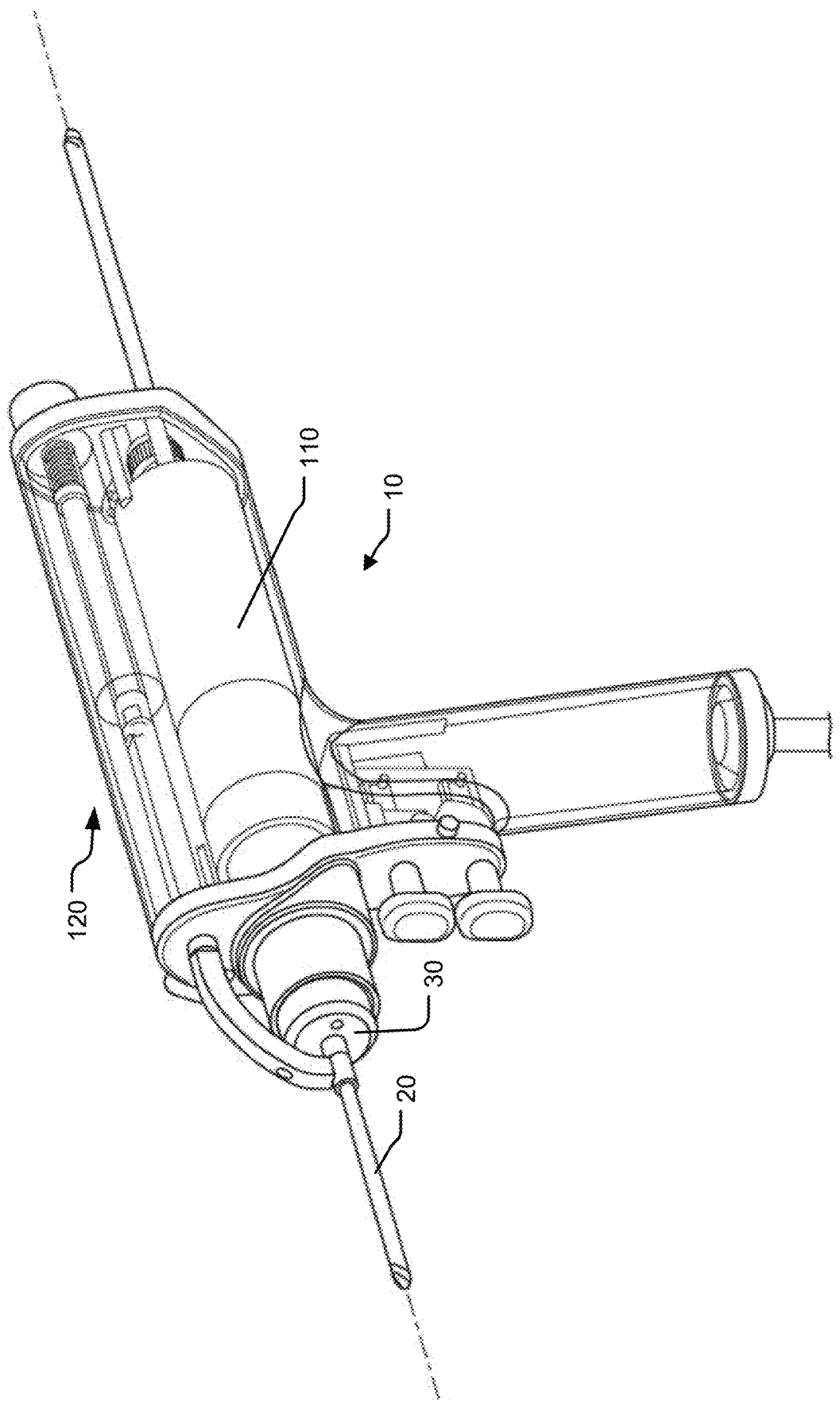
FIG. 1 illustrates an example of an instrument including an implant driver engaged with an orthopedic implant.

FIG. 1 depicts an example of an instrument 10 that may be utilized for such placement of an orthopedic implant 20. The instrument 10 may include or be engageable with an implant driver 30 to engage the orthopedic implant 20. The instrument 10 includes a drive system 110 that may be used to impart rotation to the implant driver 30. In this regard, the instrument 10 may be used to advance an orthopedic implant 20 relative to a bone of a patient and/or retract an orthopedic implant 20 from a bone of a patient.

Figure 2:
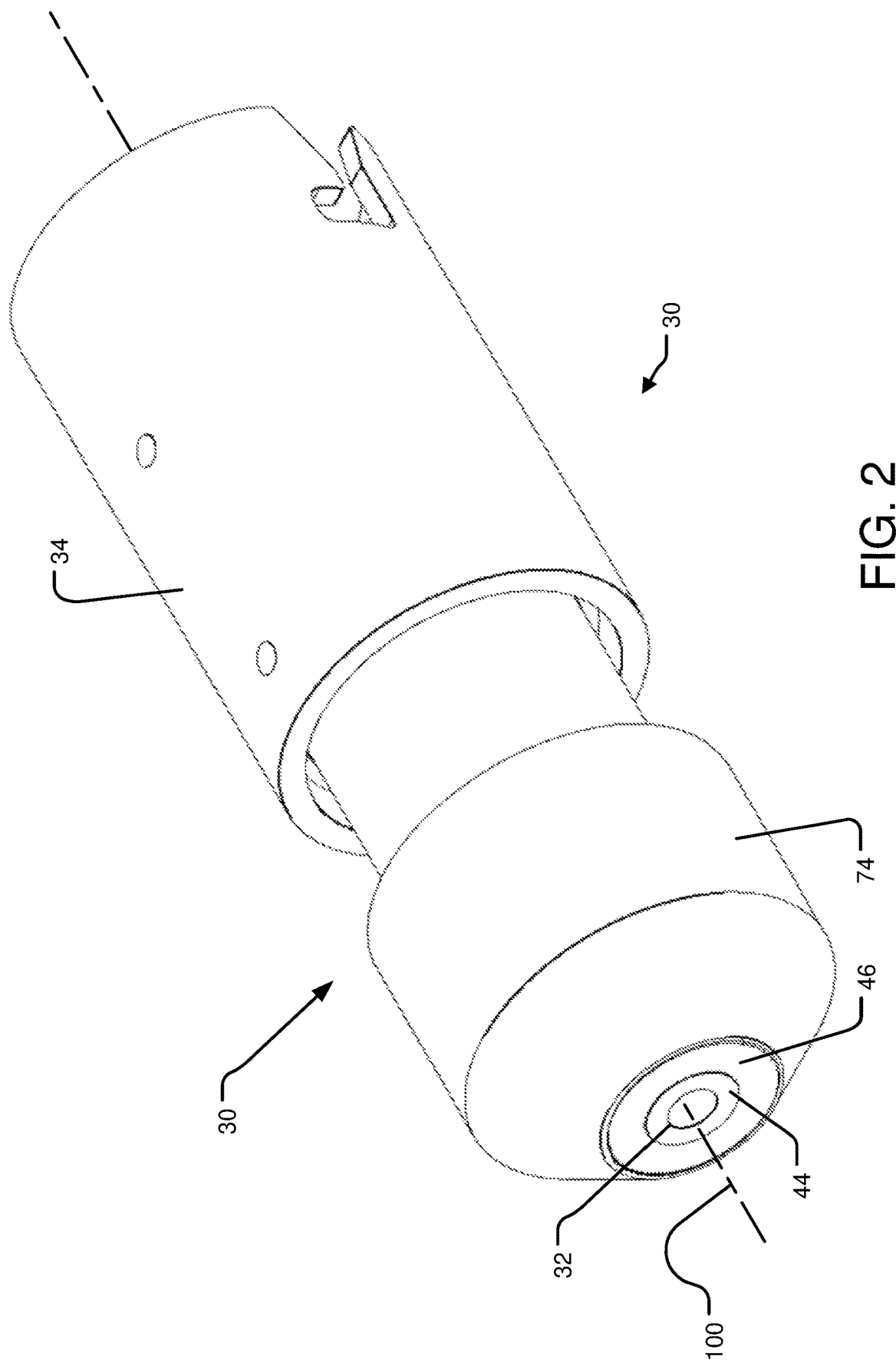
FIG. 2 illustrates a perspective view of an example implant driver.
Figure 3:
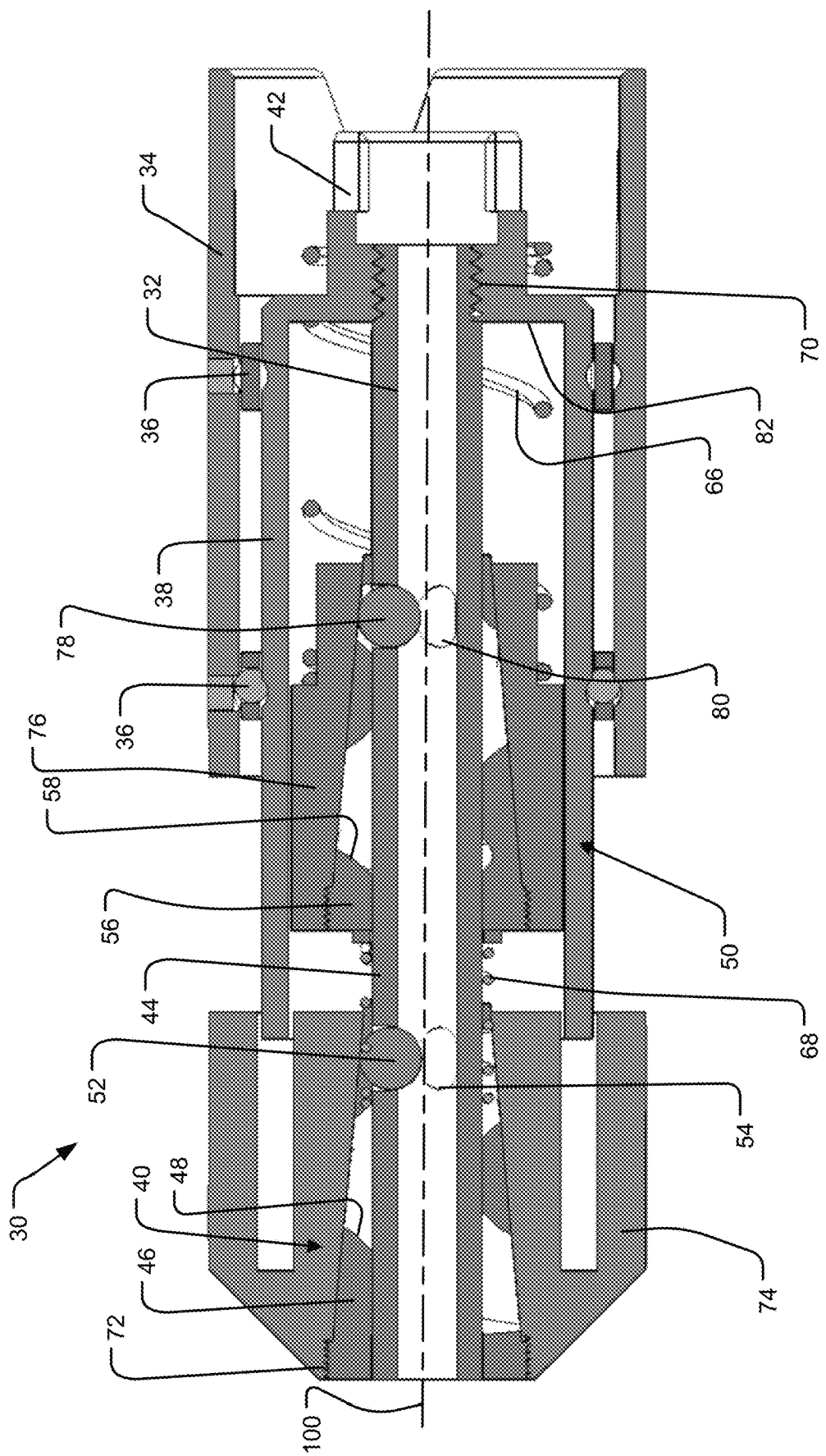
FIG. 3 illustrates a cross section view of an example implant driver taken along a working axis.
Figure 4:
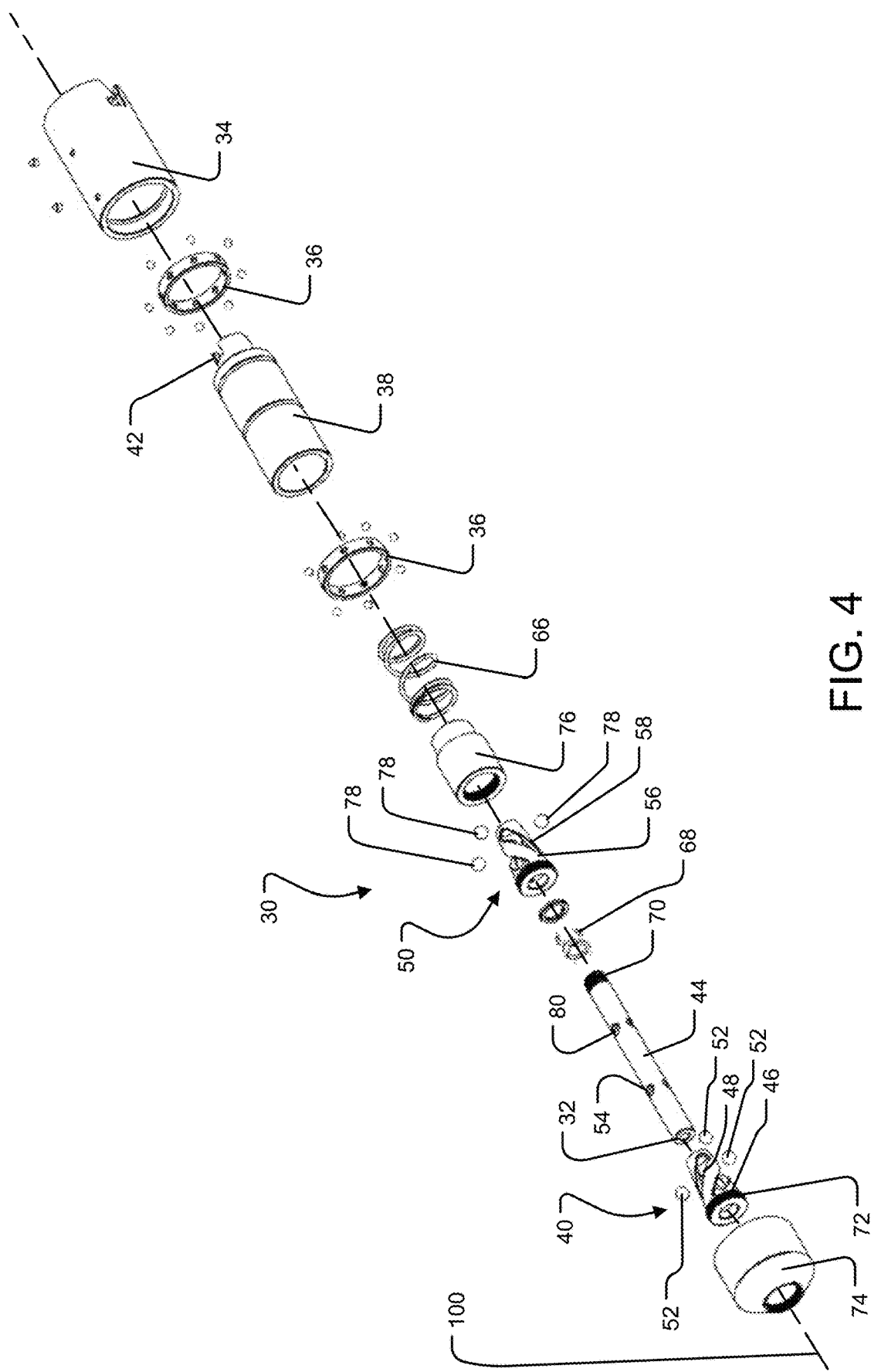
FIG. 4 illustrates an exploded view of an example of an implant driver.

FIGS. 2-4 depict the implant driver 30 in various views for explanation. FIG. 2 is a perspective view of the implant driver 30, FIG. 3 is a cross-sectional view taken along a working axis 100 of the implant driver 30, and FIG. 4 is an exploded view of the implant driver 30.

As can best be seen in FIGS. 3 and 4, the implant driver 30 may include a first jaw assembly 40 and a second jaw assembly 50. As will be described in greater detail below, the first jaw assembly 40 and/or the second jaw assembly 50 may be operative to engage an orthopedic implant 20 (not shown in FIGS. 2-4) that is disposed in a cannulated passage 32 that extends through the implant driver 30 along the working axis 100 to limit or preclude relative movement between the orthopedic implant 20 and the implant driver 30 to allow for advancement or retraction of the implant driver 30 relative to a bone of a patient. Specifically, the first jaw assembly 40 may be operative to engage an orthopedic implant 20 when the implant driver 30 is rotated by the instrument 10 in a first direction. The second jaw assembly 50 may be operative to engage an orthopedic implant 20 disposed in the cannulated passage 32 when the instrument rotates the implant driver 30 in a second direction opposite the first direction. The first jaw assembly 40 and the second jaw assembly 50 may be configured to allow an implant in the cannulated passage 32 to be moved relative to the implant driver 30 when not rotated (e.g., to allow for retraction of the implant driver 30 relative to the orthopedic implant 20). In this regard, the implant driver 30 may be used to rotate the orthopedic implant 20 in a first direction associated with a direction of advancement of the orthopedic implant 20 and in a second direction associated with a direction of retraction of the orthopedic implant 20.

The implant driver 30 includes an engagement portion 34 which may include features (described in greater detail below) that may engage corresponding engagement features of the instrument 10. This may allow the implant driver 30 to be selectively engageable and disengageable with the instrument 10 using a "quick connect/disconnect" feature for interchangeability of the implant driver 30.

One or more bearings 36 may be provided between the engagement portion 34 and a drive shaft 38 to facilitate rotation of the drive shaft 38 relative to the engagement portion 34. The drive shaft 38 may include a drive coupling 42 for engagement with the instrument 10. In turn, the drive shaft 38 may be rotated by the instrument 10 to cause rotation of the drive shaft 38. Alternatively, the drive shaft 38 and tube 44 may be integrally formed for co-rotation.

The drive shaft 38 may be threadably engaged with a threaded proximal end portion 70 of a tube 44. The tube 44 may at least partially define the cannulated passage 32 in which an orthopedic implant 20 may be disposed. In turn, upon rotation of the drive shaft 38, the tube 44 may also be rotated.

The first jaw assembly 40 may be threadably engaged with a cover 74 at a distal portion 72 of the first jaw assembly 40. The first jaw assembly 40 may include a first cam member 46. The first cam member 46 includes a first plurality of helical channels 48. The first plurality of helical channels 48 have disposed therein a first plurality of spherical jaw members 52. The spherical jaw members 52 are in contacting engagement with helical cam surfaces defined by the helical channels 48. The spherical jaw members 52 may be constrainedly moveable in a proximal and distal direction along the helical channels. The spherical jaw members 52 may also at least partially extend through corresponding holes 54 defined in the tube 44. In this regard, the spherical jaw members 52 may not move axially relative to the tube 44. In turn, as the spherical jaw members 52 move relative to the helical channels 48, the first cam member 46 may be moved axially in a proximal or distal direction relative to the tube 44.

Furthermore, the helical cam surfaces defined by the helical channels 48 are constrictive cam surfaces relative to a first direction of rotation. In this regard, as the spherical jaw members 52 move from the proximal direction to the distal direction relative to the helical channels 48, the constrictive cam surfaces of the helical channels 48 may result in the spherical jaw members 52 moving toward the working axis 100. Given the helical form of the helical channels 48, the spherical jaw members 52 may be urged toward the distal portion of the helical channels 48 when the implant driver 30 is rotated in the first direction.

The first jaw assembly 40 and the cover 74 may be moveable axially relative to the tube 44. The cover 74 may engage a stop that limits the axial travel of the cover 74 and the first jaw assembly 40 in a distal direction, while allowing proximal movement of the cover 74 and first jaw assembly 40. For instance, the interaction of the spherical jaw members 52 with the helical channels 48 may limit the axial movement of the cover 74 distally. That is, as the spherical jaw members 52 may be retained in the holes 54 in the tube 44, once the spherical jaw members 52 engage a distal portion of the helical channels 48, further proximal movement of the first cam member 46, and in turn, the cover 74 in a proximal direction is limited. Alternatively, the stop that retains the cover 74 may be a pin, lip, or other structure to limit the distal travel of the cover 74.

When the tube 44 is rotated in the first direction of rotation, the spherical jaw members 52 may interact with the helical channels 48 and be urged in a proximal direction relative to the constrictive helical cam surfaces of the helical channels 48, thus causing the spherical jaw members 52 to move toward the working axis 100 and extend into the cannulated passage 32. That is, the first cam member 46 may move distally relative to the tube 44 such that the spherical jaw members 52 are urged proximally relative to the first cam member 46 as the helical channels 48 may constrict in the proximal direction. Movement of the spherical jaw members 52 toward the constricted proximal portions of the helical channels 48 may urge the spherical jaw members 52 through the holes 54 toward the working axis 100. In turn, the spherical jaw members 52 may be urged into engagement with an implant disposed in the cannulated passage 32 by the first jaw assembly 40 when the implant driver is rotated in the first direction of rotation.

The second jaw assembly 50 may include a second cam member 56. The second cam member 56 may be threadably engaged with an axial bearing 76. The axial bearing 76 may be sized to allow for axial movement of the second jaw assembly 50 with respect to the tube 44 and an inner diameter of the drive shaft 38.

The second cam member 56 includes a second plurality of helical channels 58. The second plurality of helical channels 58 contain a second plurality of spherical jaw members 78. The spherical jaw members 78 are in contacting engagement with helical cam surfaces defined by the second plurality of helical channels 58 and may move relative to the helical channel 58 in a distal and proximal direction relative to the second cam member 56. Furthermore, the helical cam surfaces defined by the helical channels 58 define constrictive cam members relative to a second direction of rotation. In this regard, as the spherical jaw members 78 move from the proximal direction to the distal direction, the constrictive cam members of the helical channels 58 may result in the spherical jaw members 78 moving toward a working axis 100 when the implant driver is rotated in the second direction. As such, the spherical jaw members 78 also at least partially extend through holes 80 defined in the tube 44 such that the spherical jaw members 78 may extend into the cannulated passage 32, and therefore contactingly engage an orthopedic implant disposed therein.

The second cam member 56 may be moveable axially relative to the tube 44. Furthermore, the helical cam surfaces defined by the helical channels 58 define constrictive cam members relative to the second direction of rotation. The second direction of rotation is opposite the first direction of rotation. That is, when the drive shaft 38 and tube 44 are rotated in the second direction of rotation, the spherical jaw members 78 may interact with the helical channels 58 and be urged in a proximal direction relative to the constrictive helical cam surfaces. That is, the second cam member 56 may move distally relative to the tube 44 such that the spherical jaw members 78 are urged proximally relative to the second cam member 56 as the helical channels 58 may constrict in the proximal direction. Movement of the spherical jaw members 78 toward the constricted proximal portions of the helical channels 58 may urge the spherical jaw members 78 through the holes 54 toward the working axis 100. In turn, the spherical jaw members 78 may be urged into engagement with an implant disposed in the cannulated passage 32 by the second jaw assembly 50 when the implant driver is rotated in the second direction of rotation.

A first biasing member 66 may be disposed between the second jaw assembly 50 and a proximal wall 82 of the drive shaft 38. The first biasing member 66 biases the second jaw assembly 50 in a proximal direction that, in turn, urges the spherical jaw members 78 disposed in the second plurality of helical channels 58 to the constricted proximal portion thereof. The first biasing member 66 acts upon the second jaw assembly 50 even in the absence of rotation of the implant driver 30. This may result in the biasing of the spherical jaw members 78 into engagement with an orthopedic implant 20 disposed in the cannulated passage 32. However, the biasing force applied by way of the first biasing member 66 may not be great enough to preclude rotation of the spherical jaw members 78. Thus, the spherical jaw members 78 may contact and hold an implant in place absent an external force applied to the implant, but may allow the spherical jaw member 78 to be rotated to allow for movement of the implant relative to the tube 44 when an external force is applied to either the implant driver 30 or the implant. That is, the spherical jaw members 78 may hold an implant in place (e.g., relative to the force of gravity), but still allow movement between the implant and the tube 44 when the user moves the implant or the implant driver 30.

A second biasing member 68 may be disposed between the second jaw assembly 50 and the first jaw assembly 40. The second biasing member 68 biases the first jaw assembly 40 in a proximal direction that, in turn, urges the spherical jaw members 52 disposed in the first plurality of helical channels 48 to the constricted proximal portion thereof. The second biasing member 68 acts upon the first jaw assembly 40 even in the absence of rotation of the implant driver 30. This may result in the biasing of the spherical jaw members 52 into engagement with an implant disposed in the cannulated passage 32. However, the biasing force applied by way of the first 66 and/or second biasing member 68 may not be great enough to preclude rotation of the spherical jaw members 52. Thus, the spherical jaw members 52 may contact and hold an implant in place absent an external force applied to the implant, but may allow the spherical jaw member 52 to be rotated to allow for movement of the implant relative to the tube 44 when an external force is applied to either the implant driver 30 or the implant. That is, the spherical jaw members 52 may hold an implant in place (e.g., relative to the force of gravity), but still allow movement between the implant and the tube 44 when the user moves the implant or the implant driver 30.

In turn, the first biasing member 66 and the second biasing member 68 acting on the second jaw assembly 50 and first jaw assembly 40, respectively, result in the spherical jaw members 52 and 78 being urged toward the working axis 100 and into engagement with an implant disposed in the cannulated passage 32. In turn, upon rotation of the implant driver 30 in the first direction, the spherical jaw member 52 of the first jaw assembly 40 may be frictionally engaged between the cam surfaces of the first plurality of helical channels 48 and an instrument disposed in the cannulated passage 32. As the first plurality of helical channels 48 constrict corresponding to the first rotational direction, such frictional engagement may urge the spherical jaw member 52 proximally within the helical channels 48 of the first jaw assembly 40 and into greater pressure against an implant disposed in the cannulated passage 32. In contrast, the spherical jaw members 78 of the second jaw assembly 50 may initially frictionally engage the cam surfaces of the second plurality of helical channels 58 when the implant driver is rotated in the first direction. However, such frictional engagement may cause the spherical jaw members 52 of the second jaw assembly 50 to act on the second cam member 56 to urge the second jaw assembly 50 in a proximal direction to overcome the force applied by the first biasing member 66 to allow the spherical jaw members 52 to move distally in the second plurality of helical channels 58 in response to the proximal movement of the second cam member 56. The spherical jaw members 52 may move distally in the second plurality of helical channels 58 to disengage the spherical jaw members 78 from the implant. That is, when rotated in the first direction, the first jaw assembly 40 may cause the spherical jaw members 52 thereof to engage the instrument. Such action is achieved by the opposite twists of the first plurality of helical channels 48 and the second plurality of helical channels 58, respectively.

When the implant driver 30 is rotated in the second direction, the spherical jaw members 78 of the second jaw assembly 50 are engaged with the instrument while the spherical jaw member 52 of the first jaw assembly 40 are disengaged with the instrument.

As described above, the action of the first biasing member 66 and the second biasing member 68 may also supply a sufficient amount of biasing force on the spherical jaw members 52 and 78 to act as retainers for an implant disposed in the cannulated passage 32. In this regard, the spherical jaw members 52 and/or 78 may act as an implant holder that retains the implant in the cannulated passage 32 absent application of an external force to either the orthopedic implant 20 or the implant driver 30 (e.g. other than gravity). For instance, there may be occasions in which an orthopedic implant 20 may be disposed in the implant driver 30, but not engaged by the spherical jaw members 52 or 78 (e.g., when the implant driver 30 is not rotating). However, the surgeon may want the orthopedic implant to remain in its place relative to cannulated passage 32 absent movement of the orthopedic implant 20 manually by the surgeon. For example, prior to engagement of the orthopedic implant 20 by the spherical jaw members 52 or the spherical jaw members 78 of the implant driver 30, the surgeon may place the orthopedic implant in the cannulated passage 32 in a specific position. The surgeon may then move the surgical instrument without engaging the orthopedic implant 20 by rotation of the implant driver 30.

As such, the first biasing member 66 and the second biasing member 68 acting on the first jaw assembly 40 and the second jaw assembly 50 to facilitate holding an orthopedic implant 20 even in the absence of rotation of the implant driver 30. In this regard, a force by the surgeon that is manually applied to the orthopedic implant 20 to move the orthopedic implant 20 along or about the working axis 100, but absent an external force by the user, the orthopedic implant 20 remains stationary. For instance, the force of gravity may not cause the orthopedic implant 20 to slide in the cannulated passage 32 based on the engagement of the spherical jaw members 52 and 78 acting on the orthopedic implant 20 in the absence of rotation of the implant driver 30. As such, the implant driver 30 may retain the orthopedic implant 20 to help prevent axial or rotational movement of the orthopedic implant 20 relative to the implant driver 30 during use when not engaged by rotation of the implant driver 30.

It can be appreciated that use of spherical jaw members 52 and 78 allows for axial translation or rotation of the orthopedic implant 20 in relation to the implant driver 30 when not engaged by rotation of the implant driver 30. For instance, spherical jaw members 52 and 78 allow for the coefficient of friction to be relatively easy to overcome yet still is high enough to retain the orthopedic implant 20 in place when external forces are not applied. The force required by the surgeon to rotate or slide the orthopedic implant 20 about or along the axis may be equal.

Figure 8:
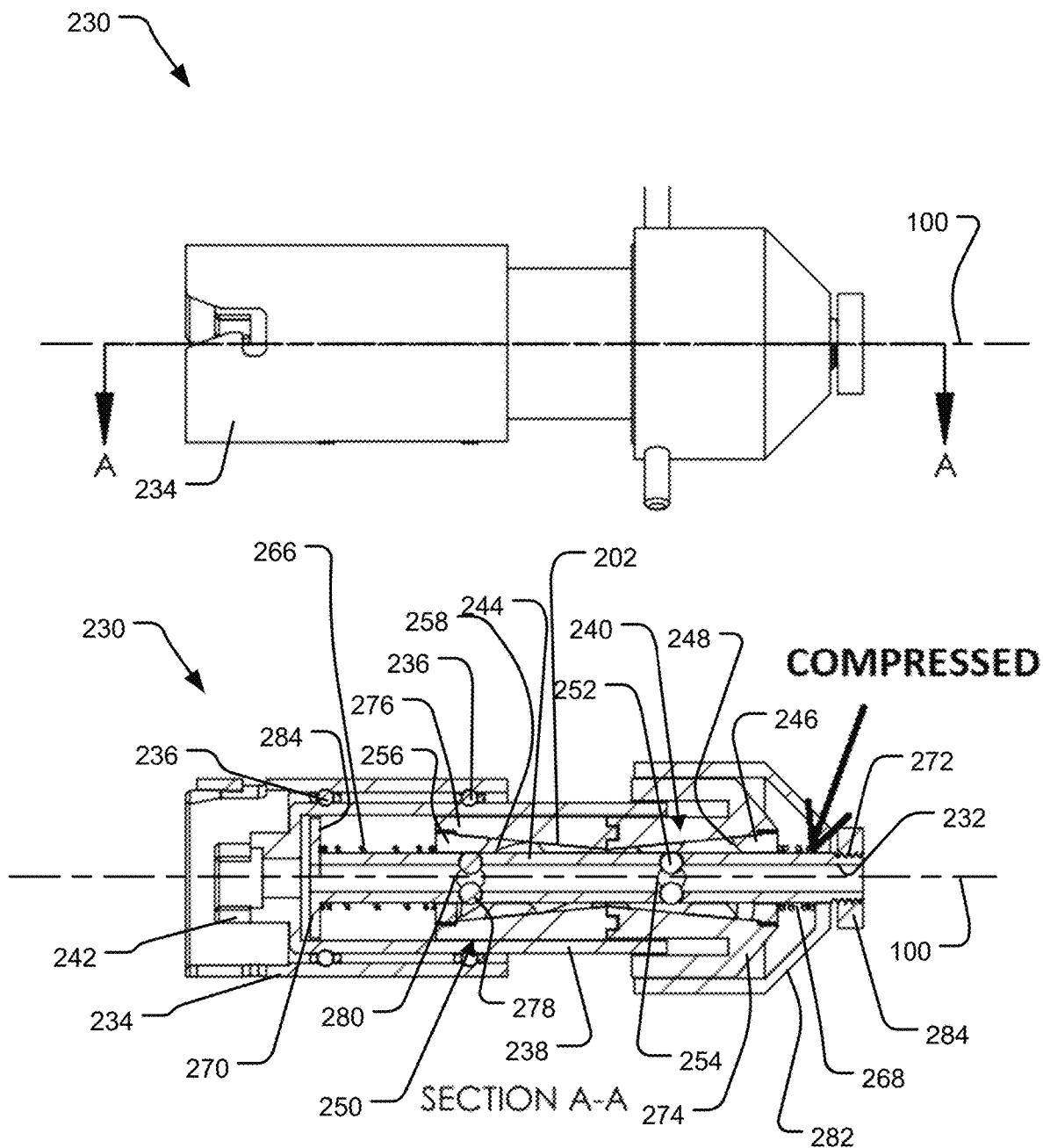
FIG. 8 illustrates an example of an implant driver with a cross sectional view in which a driver is in a first state to engage forward engagement of the implant for proximal movement of the driver and implant.
Figure 9:
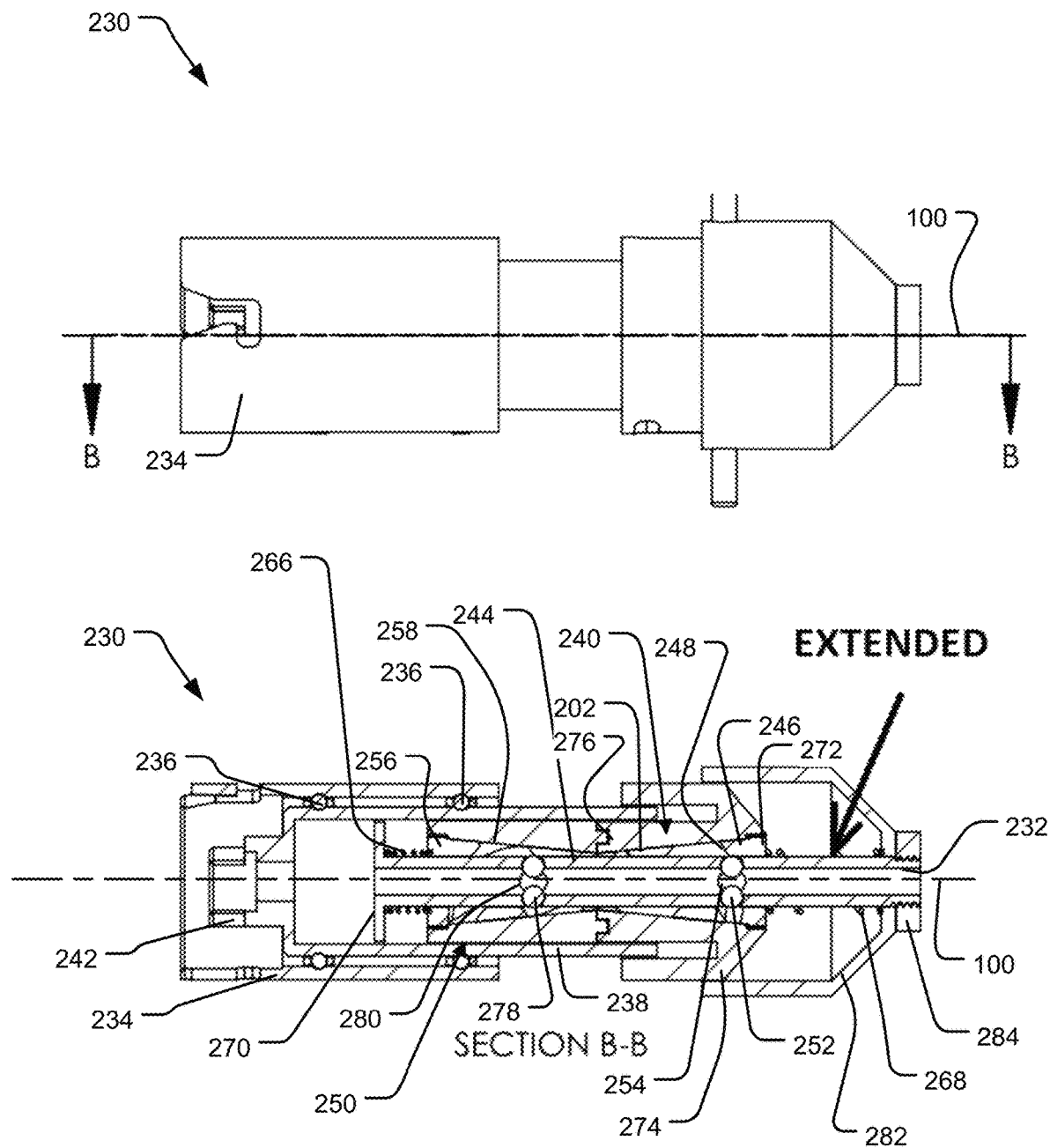
FIG. 9 illustrates an example of an implant driver with a cross sectional view in which a driver is in a second state to engage reverse engagement of the implant for distal movement of the driver and implant.

FIGS. 8 and 9 depict another embodiment of an implant driver 230. The implant driver 230 may include a first jaw assembly 240 and a second jaw assembly 250. As can be appreciated, the first jaw assembly 240 and the second jaw assembly 250 may be a distal portion and a proximal portion respectively, of a jaw body 202. That is, the jaw body 202 may be a unitary component in which the first jaw assembly 240 and the second jaw assembly 250 are incorporated. As will be described in greater detail below, the implant driver 230 may be used to rotate the orthopedic implant 20 in a first direction associated with a direction of advancement of the orthopedic implant 20 and in a second direction associated with a direction of retraction of the orthopedic implant 20.

The implant driver 230 includes an engagement portion 234 which may include features (described in greater detail below) that may engage corresponding engagement features of the instrument 10. This may allow the implant driver 230 to be selectively engageable and disengageable with the instrument 10 using a "quick connect/disconnect" feature for interchangeability of the implant driver 30.

One or more bearings 236 may be provided between the engagement portion 234 and a drive shaft 238 to facilitate rotation of the drive shaft 238 relative to the engagement portion 234. The drive shaft 238 may include a drive coupling 242 for engagement with the instrument 10. In turn, the drive shaft 238 may be rotated by the instrument 10 to cause rotation of the drive shaft 238. A tube 244 may be disposed for corotation with the drive shaft 238. The tube 244 may define at least a portion of the cannulated passage 232. In addition, the tube 244 may be moved axially relative to the jaw body 202 to dispose respective portions of the first jaw assembly 240 or the second jaw assembly 250 in engagement with the implant upon rotation of the driver 230.

The first jaw assembly 240 may be threadably engaged with a cover 274 at a distal portion 272 of the first jaw assembly 240. Additionally, the tube 244 may be threadably engaged with a shoulder 284 at the distal portion thereof. A floating member 282 may be engaged for axial movement along the tube 244 between the cover 274 and the shoulder 284. A distal portion of the tube 244 may include a flange 270. The flange 270 may limit movement of the tube 244 proximally relative to the jaw body 202.

The first jaw assembly 240 may include a first cam member 246. The first cam member 246 includes a first plurality of helical channels 248. The first plurality of helical channels 248 have disposed therein a first plurality of spherical jaw members 252. The spherical jaw members 252 are in contacting engagement with helical cam surfaces defined by the helical channels 248. The spherical jaw members 252 may be constrainedly moveable in a proximal and distal direction along the helical channels. The spherical jaw members 252 may also at least partially extend through corresponding holes 254 defined in the tube 244. In this regard, the spherical jaw members 252 may not move axially relative to the tube 244. In turn, as the spherical jaw members 252 move relative to the helical channels 248, the first cam member 246 may be moved axially in a proximal or distal direction relative to the tube 244.

Furthermore, the helical cam surfaces defined by the helical channels 248 are constrictive cam surfaces relative to a first direction of rotation. In this regard, as the spherical jaw members 252 move from the proximal direction to the distal direction relative to the helical channels 248, the constrictive cam surfaces of the helical channels 248 may result in the spherical jaw members 252 moving toward the working axis 100. Given the helical form of the helical channels 248, the spherical jaw members 252 may be urged toward the distal portion of the helical channels 248 when the implant driver 230 is rotated in the first direction.

The jaw body 202 may be engaged with a support member 276 that also engages the inner diameter of the drive shaft 238. In turn, upon rotation of the drive shaft 238, the support member 276 and the jaw body 202 may be rotated. The tube 244 may be axially moveable relative to the jaw body 202. The tube 244 may be limited in distal travel by engagement of a flange 270 with a distal end portion of the drive shaft 238. The tube 244 may be limited in proximal travel by interaction between the flange 270 and the support member 276 that is axially fixed relative to the drive shaft 238. As described in greater detail below, a distal biasing member 266 may be disposed between the flange 270 and the support member 276 and jaw body 202 to bias the flange distally relative to the support member 276 and jaw body 202. A proximal biasing member 268 may be disposed between the floating member 282 and the jaw assembly 202. The floating member 282 may be manipulated such that the relative spring force of the distal biasing member 266 and the proximal biasing member 268 are changes to influence the tube 244 relative to the jaw body 202 for selective engagement of the first jaw assembly 240 or the second jaw assembly 250.

When the tube 244 is rotated in the first direction of rotation, the spherical jaw members 252 may interact with the helical channels 248 and be urged in a proximal direction relative to the constrictive helical cam surfaces of the helical channels 248, thus causing the spherical jaw members 252 to move toward the working axis 100 and extend into the cannulated passage 232. Correspondingly, the tube 244 may be urged proximally against the biasing force of the proximal biasing member 268. The first cam member 246 may, in turn, move distally relative to the tube 244 such that the spherical jaw members 252 are urged proximally relative to the first cam member 246 as the helical channels 248 may constrict in the proximal direction. Movement of the spherical jaw members 252 toward the constricted proximal portions of the helical channels 248 may urge the spherical jaw members 252 through the holes 254 toward the working axis 100. In turn, the spherical jaw members 252 may be urged into engagement with an implant disposed in the cannulated passage 232 by the first jaw assembly 240 when the implant driver is rotated in the first direction of rotation.

The second jaw assembly 250 may include a second cam member 256. The second cam member 256 includes a second plurality of helical channels 258. The second plurality of helical channels 258 contain a second plurality of spherical jaw members 278. The spherical jaw members 278 are in contacting engagement with helical cam surfaces defined by the second plurality of helical channels 258 and may move relative to the helical channel 258 in a distal and proximal direction relative to the second cam member 256. Furthermore, the helical cam surfaces defined by the helical channels 258 define constrictive cam members relative to a second direction of rotation. In this regard, as the spherical jaw members 278 move from the distal direction to the proximal direction, the constrictive cam members of the helical channels 258 may result in the spherical jaw members 278 moving toward a working axis 100 when the implant driver is rotated in the second direction. As such, the spherical jaw members 278 also at least partially extend through holes 280 defined in the tube 244 such that the spherical jaw members 278 may extend into the cannulated passage 232, and therefore contactingly engage an orthopedic implant disposed therein.

When the second jaw assembly 250 is engaged with the implant, the tube 244 may be urged distally against the biasing force of the distal biasing member 266. The helical cam surfaces defined by the helical channels 258 define constrictive cam members relative to the second direction of rotation. The second direction of rotation is opposite the first direction of rotation. That is, when the drive shaft 238 and tube 244 are rotated in the second direction of rotation, the spherical jaw members 278 may interact with the helical channels 258 and be urged in a proximal direction relative to the constrictive helical cam surfaces. That is, the jaw body 202 may move distally relative to the tube 244 such that the spherical jaw members 278 are urged proximally relative to the second cam member 256 as the helical channels 258 may constrict in the proximal direction. Movement of the spherical jaw members 278 toward the constricted proximal portions of the helical channels 258 may urge the spherical jaw members 278 through the holes 254 toward the working axis 100. In turn, the spherical jaw members 278 may be urged into engagement with an implant disposed in the cannulated passage 232 by the second jaw assembly 250 when the implant driver is rotated in the second direction of rotation.

As described above, the distal biasing member 266 may be disposed between the jaw body 202 and a flange 270 of the tube 244. The distal biasing member 266 biases the tube 244 in a proximal direction relative to the jaw body 202 that, in turn, urges the spherical jaw members 278 disposed in the second plurality of helical channels 258 to the constricted proximal portion thereof.

A proximal biasing member 268 may be disposed between the floating member 282 and the jaw body 202. In turn, upon manipulation of the floating member 282 proximally, the spring force of the proximal biasing member 268 is increased and the tube 244 is urged proximally against the force of the proximal biasing member 266 as shown in FIG. 8. This may result in the tube 244 moving proximally, which urges the first jaw assembly 240 into engagement with the implant. Upon release of the floating member, the proximal biasing member 268 may overcome the biasing force of the distal biasing member 266, which may result in the tube 244 being moved proximally relative to the jaw body 202 to engage the second jaw assembly 250 with the implant as shown in FIG. 9.

The relative strengths of the distal biasing member 266 and the proximally biasing member 268 may be tuned to allow for selective engagement of the first jaw assembly or the second jaw assembly 250. As described above, in one embodiment, the floating member 282 may be manipulated to change the relative forces acting on the biasing members. Thus, upon movement of the floating member 282 distally, the tube 244 may be urged distally to engage the first jaw assembly 240 (e.g., for advancement of an implant upon rotation in a first direction). Releasing the floating member 282 proximally may result in the tube 244 may be urged distally by the distal biasing member 266 to engage the second jaw assembly 250 (e.g., for retraction of an implant upon rotation in a second direction). Rather than manipulation of the floating member 282, the distal biasing member 266 and the proximal biasing member 268 may be tuned relative to one another such that the relative rotation of the jaw body 202 to urge the tube 244 axially in either the proximal or distal direction upon engagement of the implant may be used to overcome the biasing forces and engage the first jaw assembly 240 or the second jaw assembly 250 upon corresponding rotation of the driver 230.

Figure 6:
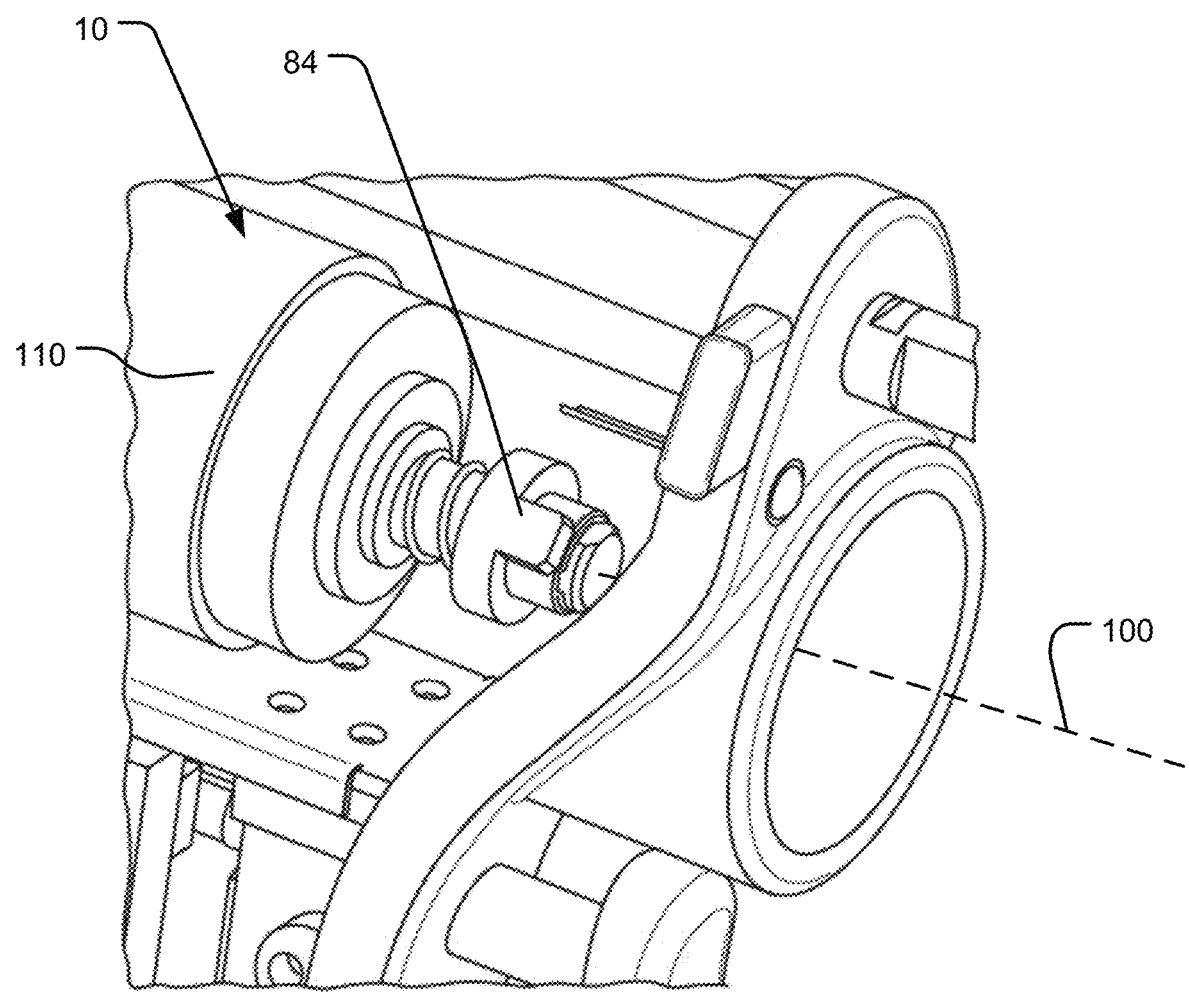
FIG. 6 illustrates an example of an implant driver interface of a surgical instrument shown in a partial cut away.

As described briefly above, an implant driver 30 may be selectively engageable and disengageable with the instrument 10. In this regard, various different chucks, drivers, or other tools may be selectively utilized in conjunction with the instrument 10. To facilitate the different chucks, the instrument 10 may provide a standardized driver engagement format to engage the various different potential embodiments of drivers 30 that may be utilized with the instrument 10. In this regard, as may be appreciated in FIG. 6, the instrument 10 may include a drive coupling 84 that engages with an implant driver 30 to impart rotational motion from the drive system 110 of the instrument 10 to the implant driver 30. In this regard, the implant driver 30 may be detachable from the instrument 10. The drive coupling 84 may be in operative communication with the drive system 110 such that the drive system 110 rotates the drive coupling 84. In turn, the drive coupling 84 may engage with the implant driver 30 to rotate at least a portion thereof (e.g., the drive shaft 38). Furthermore, the cannulated passage 32 of the implant driver 30 may be alignable with a cannulated passage of the instrument 10 when the implant driver 30 is engaged therewith.

Figure 5:
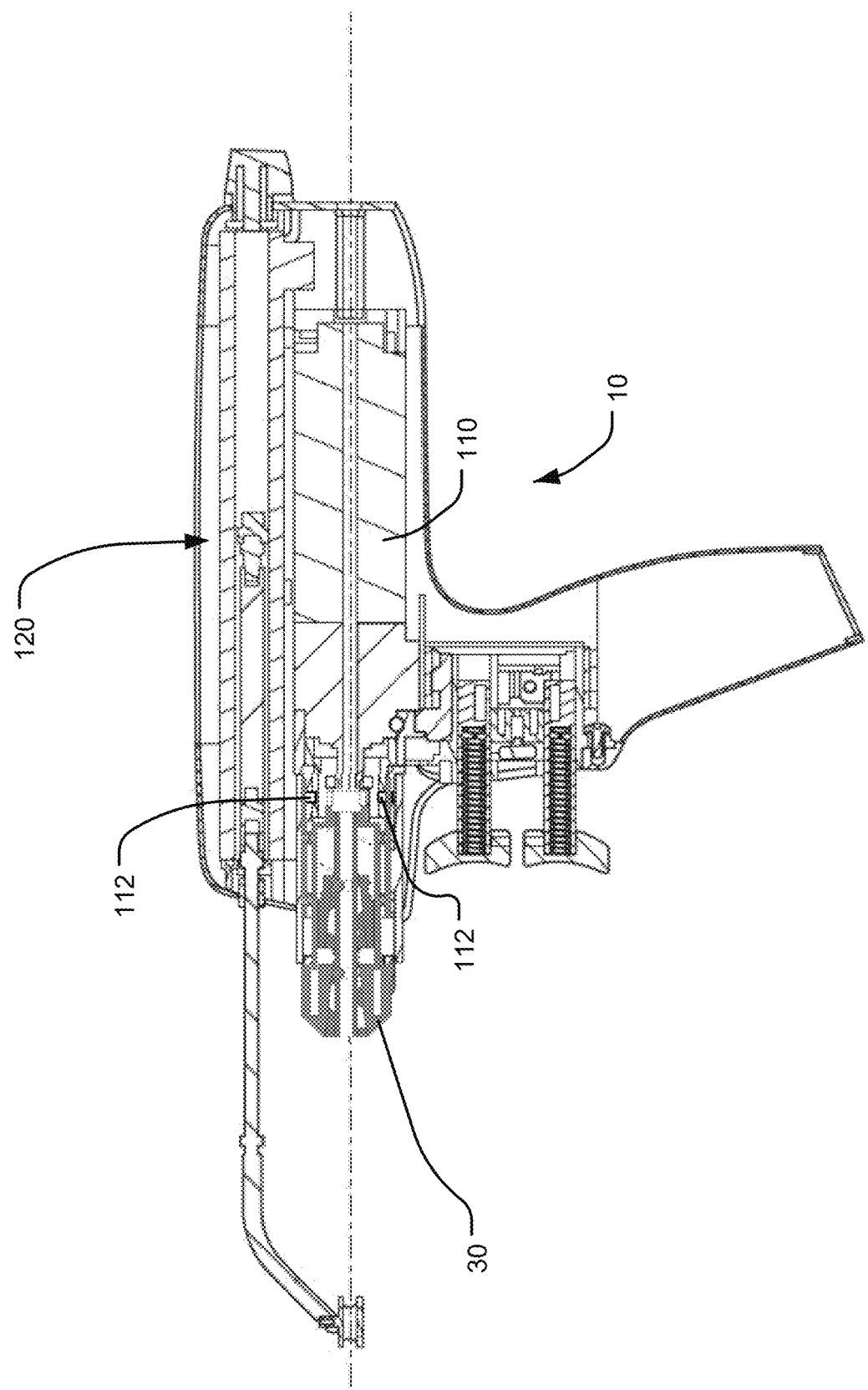
FIG. 5 illustrates a cross section view of an example instrument engaged with an implant driver.
Figure 7:
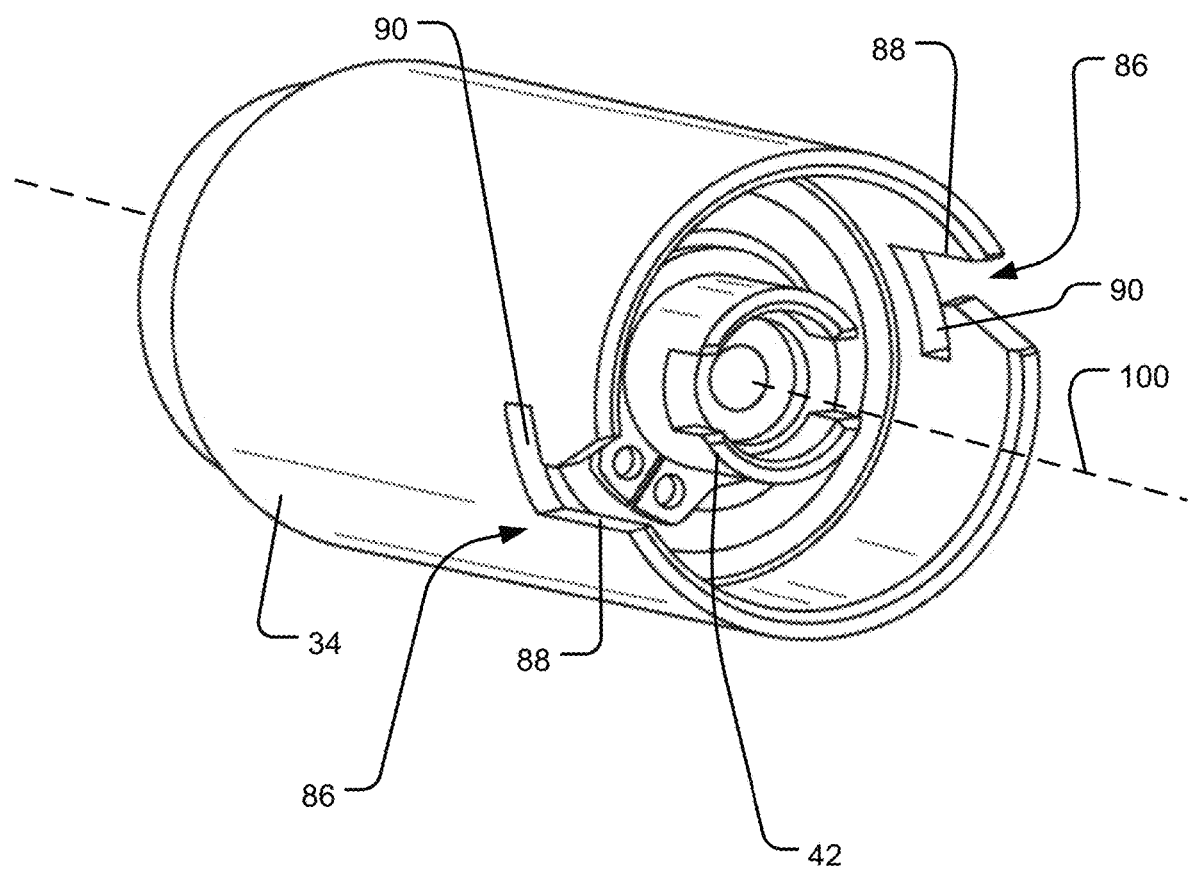
FIG. 7 illustrates an example of an implant driver for engagement with a driver interface of the surgical instrument of FIG. 6.

With further reference to FIG. 7, the proximal end of the implant driver 30 may include the drive coupling 42 discussed above disposed relative to slots 86. The slots 86 may coordinate with corresponding tabs 112 (shown in FIG. 5) provided with the instrument 10 adjacent to the drive coupling 84 to retain the implant driver 30 relative to the instrument 10. In turn, the drive coupling 42 may be keyed or otherwise configured such that the drive shaft 38 engages the drive coupling 42 of the instrument 10. In turn, the drive coupling 84 may impart rotational motion to the drive shaft 38 to rotate an orthopedic implant 20 engaged with the driver 30 as described above. The slots 86 may coordinate with the tabs to allow the implant driver 30 to be quickly attached and/or released from the instrument 10 by engagement of the slots 86 with the tabs. This may be appreciated from FIG. 7, where it is illustrated that the slots 86 may include a first portion 88 that extends parallel to the working axis 100.

The implant driver 30 may be advanced toward the drive coupling 84 along the working axis 100 such that the tabs travel along the first portion 88 of the slots 86 to the distal end thereof. The slots 86 may also include a second portion 90 that extend circumferentially about the implant driver 30. As such, once the tabs abut the distal end of the first portion 88, rotation of the driver may move the second portion 90 such that the tabs extend into the second portion 26*b*, thus restricting the implant driver 30 from movement relative to the working axis 100. That is, when the tabs are disposed in the second portion 90, the second portion 90 may be sized as to engage the tabs to limit axial movement of the implant driver 30 relative to the working axis 100. Further locking mechanisms may be provided to prevent the implant driver 30 from rotating relative to the working axis 100 when engaged so that the tabs do not slip from the second portion 90. For example, a release may be provided to lockingly maintain the implant driver 30 in position to the instrument 10 such that the implant driver 30 is only released for removal upon actuation of the release. Thus, the driver may be quickly and efficiently attached and detached from the instrument 10.

The implant driver 30 may thus be used to limit axial movement of an orthopedic implant 20 for advancement and retraction of the orthopedic implant 20 relative to the patient. In turn, the implant driver 30 may be used in conjunction with the measurement system 120 to determine a displacement of the orthopedic implant 20 relative to a reference point. Moreover, characteristics of the way the orthopedic implant 20 is advance may be monitored to assist in selective placement of the orthopedic implant 20 relative to anatomy of a patient. Such details of the use of a measurement system are disclosed in U.S. Pat. No. 10,363,078, the entirety of which is incorporated by reference herein in its entirety.

Specifically, the measurement system 120 may be able to sense proximal and distal movement of the orthopedic implant 20 relative to a reference point. However, as discussed above, absent rotation of the implant driver 30, the orthopedic implant 20 may not be axially constrained relative to the implant driver 30. In turn, measurement of any movement of the implant driver 30 by the measurement system 120 may correspond to relative movement between the orthopedic implant 20 and the implant driver 30 rather than movement of the orthopedic implant 20 relative to the patient. In turn, the measurement system 120 may only measure movement of the orthopedic implant 20 when being rotated by the drive system 110 to accurately sense relative movement between the orthopedic implant 20 and the patient when the orthopedic implant 20 is rotated to axially constrain the orthopedic implant 20 relative to the implant driver 30. In turn, sensed displacement of the orthopedic implant 20 when not being rotated may be disregarded. Moreover, only movement corresponding to proximal advancement of the implant driver 30 relative to the patient may be measured when the implant driver 30 is rotated in the first direction. Only movement corresponding to distal retraction of the implant driver 30 relative to the patient may be measured when the implant driver 30 is rotate din the second direction.

An aspect of the present disclosure relates to an implant driver engageable with a surgical instrument for use in placement of orthopedic implants relative to a bone of a patient. The driver includes a first cannulated passage extending continuously through the implant driver along a working axis. The first cannulated passage is sized to receive and extend about at least a portion of an orthopedic implant within the cannulated passage. The driver also includes a first jaw assembly. The first jaw assembly includes a plurality of first helical channels comprising a first constrictive helical cam surface with a first direction of constriction associated with a first direction of rotation of the implant driver. The first jaw assembly also includes a plurality of first spherical jaw members each disposed within a respective one of the plurality of first helical channels such that at least a portion of each of the first spherical jaw members is at least partially extendable into the cannulated passage to engage the orthopedic implant. The driver also includes a second jaw assembly. The second jaw assembly has a plurality of second helical channels comprising a second constrictive helical cam surface with a second direction of constriction associated with a second direction of rotation of the implant driver opposite the first direction of rotation. The second jaw assembly also includes a plurality of second spherical jaw members each disposed within a respective one of the plurality of second helical channels such that at least a portion of each of the second spherical jaw members is at least partially extendable into the cannulated passage to directly engage the orthopedic implant. In turn, upon rotational motion of the implant driver in the first direction of rotation, rotational motion of the first helical channels engage the first constrictive helical cam surface with the first spherical jaw members to urge the first spherical jaw members into direct engagement with the orthopedic implant. Furthermore, upon rotational motion of the implant driver in the second direction of rotation, rotational motion of the second helical channels engage the second constrictive helical cam surface with the second spherical jaw members to urge the second spherical jaw members into direct engagement with the orthopedic implant.

In an example of the driver, the first plurality of spherical jaw members comprise an implant holder displaceable relative to the cannulated passage to retain the orthopedic implant. The first constrictive helical cam surface may be normally biased into engagement with the plurality of first spherical jaw members to dispose the spherical jaw members toward the working axis to directly engage the orthopedic implant. In turn, upon insertion of the orthopedic implant, the orthopedic implant displaces the first spherical jaw members away from the working axis in a direction radial to the working axis and the first spherical jaw members bear on the orthopedic implant in a direction radially toward the working axis.

In another example of the driver, the implant driver is retractable relative to the orthopedic implant in the absence of rotational movement of the implant driver.

In yet another example, the first direction of rotation corresponds to a direction of advancement of the orthopedic implant and the second direction of rotation corresponds to a direction of withdrawal of the orthopedic implant.

In another example, the first jaw assembly and the second jaw assembly may be portions of a unitary jaw body. Furthermore, a tube may be axially moveable relative to the jaw body upon engagement of the plurality of first spherical jaw members or the plurality of second spherical jaw members. In an example, the driver may also include a distal biasing member to bias the tube proximally relative to the jaw body and a proximal biasing member to bias the tube distally relative to the jaw body. In turn, upon rotation of the implant driver in the first direction, the tube may be urged distally against a distal biasing force of the distal biasing member to urge the first plurality of spherical jaw members into the cannulated passage to engage the orthopedic implant. Also, upon rotation of the implant driver in the second direction, the tube may be urged proximally against a proximal biasing force of the proximal biasing member to urge the second plurality of spherical jaw members into the cannulated passage to engage the orthopedic implant. The driver may also include a floating member that is axially manipulable to alter the relative force acting on the tube by the proximal biasing member and the distal biasing member.

Another aspect of the present disclosure includes an orthopedic surgical system. The system includes an implant driver according to any of the examples provided above. In addition, the system includes a surgical instrument with which the implant driver is engaged and a measurement system of the surgical instrument operative to measure relative movement of an implant engaged with the implant driver relative to a reference point. The measurement system only measures the relative movement of the implant when the implant driver is rotated by the surgical instrument.

In an example of the system, the measurement system measures proximal advancement of the implant when the implant driver is rotated in the first direction of rotation and measures distal retraction of the implant when the implant driver is rotated in the second direction of rotation.

Another aspect includes a method of use of an implant driver. The method includes engaging an implant driver with a surgical instrument and rotating the implant driver in a first direction of rotation to engage an implant disposed in a cannulated passage of the implant driver in response to the rotation in the first direction. The method also includes rotating the implant driver in a second direction of rotation opposite the first direction of rotation to engage the implant disposed in the cannulated passage of the implant driver in response to the rotation in the second direction. Furthermore, the method includes, in the absence of rotation of the implant driver, allowing the implant to be axially displaced relative to the implant driver at least in response to application of an external force.

In an example, the rotating the implant driver in a first direction of rotation may include urging a plurality of first spherical jaw members each disposed within a respective one of a plurality of first helical channels such that at least a portion of each of the first spherical jaw members is at least partially extendable into the cannulated passage to engage an implant disposed in the cannulated passage of the implant driver in response to the rotation in the first direction. Also, the rotating the implant driver in a second direction of rotation opposite the first direction of rotation may include urging a plurality of second spherical jaw members each disposed within a respective one of a plurality of second helical channels such that at least a portion of each of the second spherical jaw members is at least partially extendable into the cannulated passage to engage the implant disposed in the cannulated passage of the implant driver in response to the rotation in the second direction.

In an example, at least one of the rotation the implant driver in the first direction or the rotation the implant driver in the second direction further comprises overcoming a biasing force of a biasing member to induce relative axial movement between a jaw assembly and a tube to dispose a respective one of the plurality of first spherical jaw members or the plurality of second spherical jaw members into the cannulated passage to engage the implant disposed in the cannulated passage of the implant driver. In turn, the method may also include urging the tube distally against a distal biasing force of a distal biasing member to urge the first plurality of spherical jaw members into the cannulated passage to engage the implant upon rotation of the implant driver in the first direction. Furthermore, the method may include urging the tube proximally against a proximal biasing force of a proximal biasing member to urge the second plurality of spherical jaw members into the cannulated passage to engage the implant upon rotation of the implant driver in the second direction.

In an example, the method may include manipulating a floating member axially in one of a proximal or distal direction to alter the relative force acting on the tube by the proximal biasing member and the distal biasing member. In another example, engagement of the implant disposed in the cannulated passage may be in response to one of the rotation in the first direction of rotation or the rotation in the second direction of rotation in the absence of an external force applied to the implant driver by a user.

In an example of the method, measuring proximal displacement of the implant relative to a reference point when the implant driver is rotated in the first direction also occurs. Furthermore, the method may include measuring distal retraction of the implant relative to the reference point when the implant driver is rotated in the second direction.

The implementations described herein are implemented as logical steps in one or more computer systems. The logical operations may be implemented (1) as a sequence of processor-implemented steps executing in one or more computer systems and (2) as interconnected machine or circuit modules within one or more computer systems. The implementation is a matter of choice, dependent on the performance requirements of the computer system being utilized. Accordingly, the logical operations making up the implementations described herein are referred to variously as operations, steps, objects, or modules. Furthermore, it should be understood that logical operations may be performed in any order, unless explicitly claimed otherwise or a specific order is inherently necessitated by the claim language.

What is claimed is:

1. An implant driver engageable with a surgical instrument for use in placement of orthopedic implants relative to a bone of a patient, the driver comprising:
    a first cannulated passage extending continuously through the implant driver along a working axis, the first cannulated passage being sized to receive and extend about at least a portion of an orthopedic implant within the cannulated passage;
    a first jaw assembly comprising:
        a plurality of first helical channels comprising a first constrictive helical cam surface with a first direction of constriction associated with a first direction of rotation of the implant driver, and
        a plurality of first spherical jaw members each disposed within a respective one of the plurality of first helical channels such that at least a portion of each of the first spherical jaw members is at least partially extendable into the cannulated passage to engage the orthopedic implant;
    a second jaw assembly comprising:
        a plurality of second helical channels comprising a second constrictive helical cam surface with a second direction of constriction associated with a second direction of rotation of the implant driver opposite the first direction of rotation, and
        a plurality of second spherical jaw members each disposed within a respective one of the plurality of second helical channels such that at least a portion of each of the second spherical jaw members is at least partially extendable into the cannulated passage to directly engage the orthopedic implant; and
    wherein, upon rotational motion of the implant driver in the first direction of rotation, rotational motion of the first helical channels engage the first constrictive helical cam surface with the first spherical jaw members to urge the first spherical jaw members into direct engagement with the orthopedic implant, and, upon rotational motion of the implant driver in the second direction of rotation, rotational motion of the second helical channels engage the second constrictive helical cam surface with the second spherical jaw members to urge the second spherical jaw members into direct engagement with the orthopedic implant.

2. The driver of claim 1, wherein the first plurality of spherical jaw members comprise an implant holder displaceable relative to the cannulated passage to retain the orthopedic implant.

3. The driver of claim 2, wherein the first constrictive helical cam surface is normally biased into engagement with the plurality of first spherical jaw members to dispose the spherical jaw members toward the working axis to directly engage the orthopedic implant.

4. The driver of claim 3, wherein upon insertion of the orthopedic implant, the orthopedic implant displaces the first spherical jaw members away from the working axis in a direction radial to the working axis and the first spherical jaw members bear on the orthopedic implant in a direction radially toward the working axis.

5. The driver of claim 1, wherein the implant driver is retractable relative to the orthopedic implant in the absence of rotational movement of the implant driver.

6. The driver of claim 1, wherein the first direction of rotation corresponds to a direction of advancement of the orthopedic implant and the second direction of rotation corresponds to a direction of withdrawal of the orthopedic implant.

7. The driver of claim 1, wherein the first jaw assembly and the second jaw assembly are portions of a unitary jaw body.

8. The driver of claim 7, wherein a tube is axially moveable relative to the jaw body upon engagement of the plurality of first spherical jaw members or the plurality of second spherical jaw members.

9. The driver of claim 8, further comprising:
    a distal biasing member to bias the tube proximally relative to the jaw body; and
    a proximal biasing member to bias the tube distally relative to the jaw body.

10. The driver of claim 9, wherein:
    upon rotation of the implant driver in the first direction, the tube is urged distally against a distal biasing force of the distal biasing member to urge the first plurality of spherical jaw members into the cannulated passage to engage the orthopedic implant; and
    upon rotation of the implant driver in the second direction, the tube is urged proximally against a proximal biasing force of the proximal biasing member to urge the second plurality of spherical jaw members into the cannulated passage to engage the orthopedic implant.

11. The driver of claim 10, further comprising:
    a floating member that is axially manipulable to alter the relative force acting on the tube by the proximal biasing member and the distal biasing member.

12. An orthopedic surgical system, comprising:
    an implant driver comprising:
        a first cannulated passage extending continuously through the implant driver along a working axis, the first cannulated passage being sized to receive and extend about at least a portion of an orthopedic implant within the cannulated passage;
        a first jaw assembly comprising:
            a plurality of first helical channels comprising a first constrictive helical cam surface with a first direction of constriction associated with a first direction of rotation of the implant driver, and
            a plurality of first spherical jaw members each disposed within a respective one of the plurality of first helical channels such that at least a portion of each of the first spherical jaw members is at least partially extendable into the cannulated passage to engage the orthopedic implant;
        a second jaw assembly comprising:
            a plurality of second helical channels comprising a second constrictive helical cam surface with a second direction of constriction associated with a second direction of rotation of the implant driver opposite the first direction of rotation, and a plurality of second spherical jaw members each disposed within a respective one of the plurality of second helical channels such that at least a portion of each of the second spherical jaw members is at least partially extendable into the cannulated passage to directly engage the orthopedic implant; and wherein, upon rotational motion of the implant driver in the first direction of rotation, rotational motion of the first helical channels engage the first constrictive helical cam surface with the first spherical jaw members to urge the first spherical jaw members into direct engagement with the orthopedic implant, and, upon rotational motion of the implant driver in the second direction of rotation, rotational motion of the second helical channels engage the second constrictive helical cam surface with the second spherical jaw members to urge the second spherical jaw members into direct engagement with the orthopedic implant, a surgical instrument with which the implant driver is engaged; and a measurement system of the surgical instrument operative to measure relative movement of an implant engaged with the implant driver relative to a reference point, wherein the measurement system only measures the relative movement of the implant when the implant driver is rotated by the surgical instrument.

13. The orthopedic surgical system of claim 12, wherein the measurement system measures proximal advancement of the implant when the implant driver is rotated in the first direction of rotation and measures distal retraction of the implant when the implant driver is rotated in the second direction of rotation.

* * * * *